United States Patent
Stolen et al.

(10) Patent No.: US 11,963,756 B2
(45) Date of Patent: Apr. 23, 2024

(54) COVID-19 REMOTE MONITORING

(71) Applicant: Cardiac Pacemakers, Inc., St. Paul, MN (US)

(72) Inventors: Craig Stolen, New Brighton, MN (US); Pramodsingh Hirasingh Thakur, Woodbury, MN (US); Rezwan Ahmed, Arden Hills, MN (US); Viktoria A. Averina, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 199 days.

(21) Appl. No.: 17/468,969

(22) Filed: Sep. 8, 2021

(65) Prior Publication Data

US 2022/0071507 A1 Mar. 10, 2022

Related U.S. Application Data

(60) Provisional application No. 63/076,282, filed on Sep. 9, 2020.

(51) Int. Cl.
*A61B 5/08* (2006.01)
*A61B 5/00* (2006.01)
*A61B 5/01* (2006.01)

(52) U.S. Cl.
CPC .......... *A61B 5/0816* (2013.01); *A61B 5/0004* (2013.01); *A61B 5/01* (2013.01); *A61B 5/48* (2013.01)

(58) Field of Classification Search
CPC ....... A61B 5/0816; A61B 5/01; A61B 5/0878; A61B 5/0004; A61B 5/02055; A61B 5/02416; A61B 5/0535; A61B 5/11; A61B 5/4561; A61B 5/48; A61B 5/686; A61B 5/7264; A61B 5/7282; A61B 5/742; A61B 5/746; A61H 3/00; A45B 2200/05
See application file for complete search history.

(56) References Cited

U.S. PATENT DOCUMENTS

| | | | |
|---|---|---|---|
| 11,504,011 B1 * | 11/2022 | Jain | G06N 5/04 |
| 11,783,947 B2 * | 10/2023 | Abeyratne | G16H 10/20 600/529 |
| 2016/0220127 A1 * | 8/2016 | Boyer | A61B 5/02055 |
| 2021/0077035 A1 * | 3/2021 | Kayser | A61B 5/7225 |
| 2021/0369196 A1 * | 12/2021 | Ahmed | A61B 5/4842 |
| 2021/0407684 A1 * | 12/2021 | Pho | A61B 5/7267 |

* cited by examiner

*Primary Examiner* — May A Abouelela
*Assistant Examiner* — Anna Roberts
(74) *Attorney, Agent, or Firm* — Schwegman Lundberg & Woessner. P.A.

(57) ABSTRACT

Systems and methods to provide remote patient monitoring for viral-respiratory symptoms, including coronavirus or COVID-19 symptoms are disclosed, including a signal receiver circuit configured to receive first and second physiologic information of a patient, the first physiologic information comprising respiration rate information of a patient and the second physiologic information different than the first physiologic information, and an assessment circuit configured to determine an indication of patient viral-respiratory disease using the received first and second physiologic information.

18 Claims, 4 Drawing Sheets

US 11,963,756 B2

COVID-19 REMOTE MONITORING

CLAIM OF PRIORITY

This application claims the benefit of priority under 35 U.S.C. § 119(e) of U.S. Provisional Patent Application Ser. No. 63/076,282, filed on Sep. 9, 2020, which is herein incorporated by reference in its entirety.

TECHNICAL FIELD

This document relates generally to remote patient monitoring, and more particularly, but not by way of limitation, to systems and methods to provide remote patient monitoring for viral-respiratory symptoms, including symptoms associated with coronavirus or COVID-19.

BACKGROUND

Medical devices can be implanted or implantable in a body of a patient, such as to monitor patients, including detecting or sensing physiologic information from the patient, such as one or more of heart sounds, respiration (e.g., respiration rate (RR), tidal volume (TV), etc.), impedance (e.g., thoracic impedance, cardiac impedance, cutaneous impedance, etc.), pressure (e.g., blood pressure), cardiac activity (e.g., heart rate, cardiac electrical information, etc.), chemical (e.g., electrolyte), physical activity, posture, plethysmography, or one or more other physiologic information of the patient, and, in certain examples, provide therapy to the patient in clinical and ambulatory settings. Implantable medical devices (IMDs) can include cardiac rhythm management (CRM) devices, such as pacemakers, cardiac resynchronization devices, cardioverters, cardiac monitors, defibrillators, drug delivery devices, or one or more other IMDs implanted or implantable within a body of, or subcutaneously to, a patient.

Ambulatory medical devices (AMDs), including implantable, subcutaneous, wearable, external, or one or more other medical devices, etc., can monitor, detect, or treat various conditions, including heart failure (HF), atrial fibrillation (AF), etc. AMDs may include sensors to sense physiological signals from a patient. Frequent patient monitoring by AMDs can increase early detection of worsening patient condition, including viral-respiratory disorders, such as coronavirus, COVID-19, etc., may help improve patient outcome. Identification of patients or groups of patients at an elevated risk of future adverse events may help provide timely patient treatment or prevent or reduce patient hospitalization. Identifying and safely managing patient risk of worsening condition may avoid unnecessary medical interventions or hospitalizations and reduce healthcare costs.

SUMMARY

Systems and methods to provide remote patient monitoring for viral-respiratory symptoms, including coronavirus or COVID-19 symptoms are disclosed, including a signal receiver circuit configured to receive first and second physiologic information of a patient, the first physiologic information comprising respiration rate information of a patient and the second physiologic information different than the first physiologic information, and an assessment circuit configured to determine an indication of patient viral-respiratory disease using the received first and second physiologic information.

An example (e.g., "Example 1") of subject matter (e.g., a system) may comprise a signal receiver circuit configured to receive first and second physiologic information of a patient, the first physiologic information comprising respiration rate information of the patient, and the second physiologic information different than the first physiologic information, and an assessment circuit configured to determine an indication of patient viral-respiratory disease using the received first and second physiologic information.

In Example 2, the subject matter of Example 1 may optionally be configured such that the assessment circuit is configured to determine the indication of patient viral-respiratory disease using a difference in a rate of change of the first physiologic information to the second physiologic information.

In Example 3, the subject matter of any one or more of Examples 1-2 may optionally be configured such that the assessment circuit is configured to determine the indication of patient viral-respiratory disease using the second physiologic information in response to the first physiologic information meeting a predetermined criterion.

In Example 4, the subject matter of any one or more of Examples 1-3 may optionally be configured such that the assessment circuit is configured to determine the indication of patient viral-respiratory disease using the first physiologic information of a first time period and the second physiologic information of a second time period different than the first time period.

In Example 5, the subject matter of any one or more of Examples 1-4 may optionally be configured such that the first time period precedes and is non-overlapping with the second time period.

In Example 6, the subject matter of any one or more of Examples 1-5 may optionally be configured such that the second physiologic information comprises temperature information of the patient and the assessment circuit is configured to determine the indication of patient viral-respiratory disease as a function of an increase in the temperature information of the patient in response to a relative increase in the respiration rate information of the patient exceeding a threshold amount.

In Example 7, the subject matter of any one or more of Examples 1-6 may optionally be configured such that the assessment circuit is configured to determine the relative increase in the respiration rate information using a difference between the received respiration rate information of the patient and a respiration rate baseline of the patient, wherein the threshold amount is a function of the respiration rate baseline, the increase in the temperature information comprises a relative increase the temperature information, and the assessment circuit is configured to determine the relative increase in the temperature information using a difference between the received temperature information of the patient and a temperature baseline of the patient.

In Example 8, the subject matter of any one or more of Examples 1-7 may optionally be configured such that the assessment circuit is configured to determine the respiration rate baseline of the patient using the received respiration rate information of the patient over a first time period, and to determine the temperature baseline of the patient using the received respiration rate information of the patient over a second time period.

In Example 9, the subject matter of any one or more of Examples 1-8 may optionally be configured such that the system comprises an ambulatory medical device comprising a respiration sensor configured to sense respiration information of the patient, wherein the ambulatory medical device is configured to adjust a behavior of the ambulatory medical device based on a change in the determined indication of patient viral-respiratory disease.

An example (e.g., "Example 10") of subject matter (e.g., a method) may comprise receiving, using a signal receiver circuit, first and second physiologic information of a patient, the first physiologic information comprising respiration rate information of the patient, and the second physiologic information different than the first physiologic information, and determining, using an assessment circuit, an indication of patient viral-respiratory disease using the received first and second physiologic information.

In Example 11, the subject matter of any one or more of Examples 1-10 may optionally be configured such that the determining the indication of patient viral-respiratory disease comprises using a difference in a rate of change of the first physiologic information to the second physiologic information.

In Example 12, the subject matter of any one or more of Examples 1-11 may optionally be configured such that the determining the indication of patient viral-respiratory disease comprises using the second physiologic information in response to the first physiologic information meeting a predetermined criterion.

In Example 13, the subject matter of any one or more of Examples 1-12 may optionally be configured such that the determining the indication of patient viral-respiratory disease comprises using the first physiologic information of a first time period and the second physiologic information of a second time period different than the first time period.

In Example 14, the subject matter of any one or more of Examples 1-13 may optionally be configured such that the first time period precedes and is non-overlapping with the second time period.

In Example 15, the subject matter of any one or more of Examples 1-14 may optionally be configured such that the second physiologic information comprises temperature information of the patient, and the determining the indication of patient viral-respiratory disease comprises as a function of an increase in the temperature information of the patient in response to a relative increase in the respiration rate information of the patient exceeding a threshold amount.

In Example 16, the subject matter of any one or more of Examples 1-15 may optionally be configured such that the determining the relative increase in the respiration rate information comprises using a difference between the received respiration rate information of the patient and a respiration rate baseline of the patient, wherein the threshold amount is a function of the respiration rate baseline, the increase in the temperature information comprises a relative increase the temperature information, and the assessment circuit is configured to determine the relative increase in the temperature information using a difference between the received temperature information of the patient and a temperature baseline of the patient.

In Example 17, the subject matter of any one or more of Examples 1-16 may optionally comprise determining, using the assessment circuit, the respiration rate baseline of the patient using the received respiration rate information of the patient over a first time period, and determining, using the assessment circuit, the temperature baseline of the patient using the received respiration rate information of the patient over a second time period.

In Example 18, the subject matter of any one or more of Examples 1-17 may optionally comprise sensing, using a respiration sensor of an ambulatory medical device, respiration information of the patient and determining the respiration rate information of the patient, adjusting, using a control circuit of the ambulatory medical device, a behavior of the ambulatory medical device based on a change in the determined indication of patient viral-respiratory disease.

An example (e.g., "Example 19") of subject matter (e.g., a system) may comprise means for receiving first and second physiologic information of a patient, the first physiologic information comprising respiration rate information of the patient, and the second physiologic information different than the first physiologic information and means for determining an indication of patient viral-respiratory disease using the received first and second physiologic information.

In Example 20, the subject matter of any one or more of Examples 1-19 may optionally be configured such that the second physiologic information comprises temperature information of the patient, and the means for determining the indication of patient viral-respiratory disease using the received first and second physiologic information comprises means for determining the indication of patient viral-respiratory disease as a function of an increase in the temperature information of the patient in response to a relative increase in the respiration rate information of the patient exceeding a threshold amount.

In Example 21, subject matter (e.g., a system or apparatus) may optionally combine any portion or combination of any portion of any one or more of Examples 1-20 to comprise "means for" performing any portion of any one or more of the functions or methods of Examples 1-20, or at least one "non-transitory machine-readable medium" including instructions that, when performed by a machine, cause the machine to perform any portion of any one or more of the functions or methods of Examples 1-20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The coronavirus disease 2019 (COVID-19) is an infectious viral-respiratory disease caused by severe acute respiratory syndrome coronavirus 2 (SARS-CoV-2). During population spread of infectious disease, tools are needed to remotely monitor at-risk patient populations for the benefit of individual infected patients, as well as to monitor spread of the disease and its impact across patient populations.

AMDs, including CRM devices, are commonly implanted in or associated with patients having cardiovascular conditions or risks of cardiovascular conditions. Such devices include implantable or ambulatory sensors for remote patient monitoring. Individuals with underlying cardiovascular comorbidities are at particular risk of COVID-19.

The present inventors have recognized, among other things, a unique signature of sensor changes to identify subjects with active viral infections and distinguish such conditions from one or more other adverse medical events, in certain examples, prior to detecting a rise in patient temperature or one or more other early detectable viral-respiratory disease indicators. The systems and methods disclosed herein allow existing devices and sensors to triage patients without the need for patients to visit clinics and can provide management and direction of screened patients to testing sites or hospitals for treatment.

Figure 1:
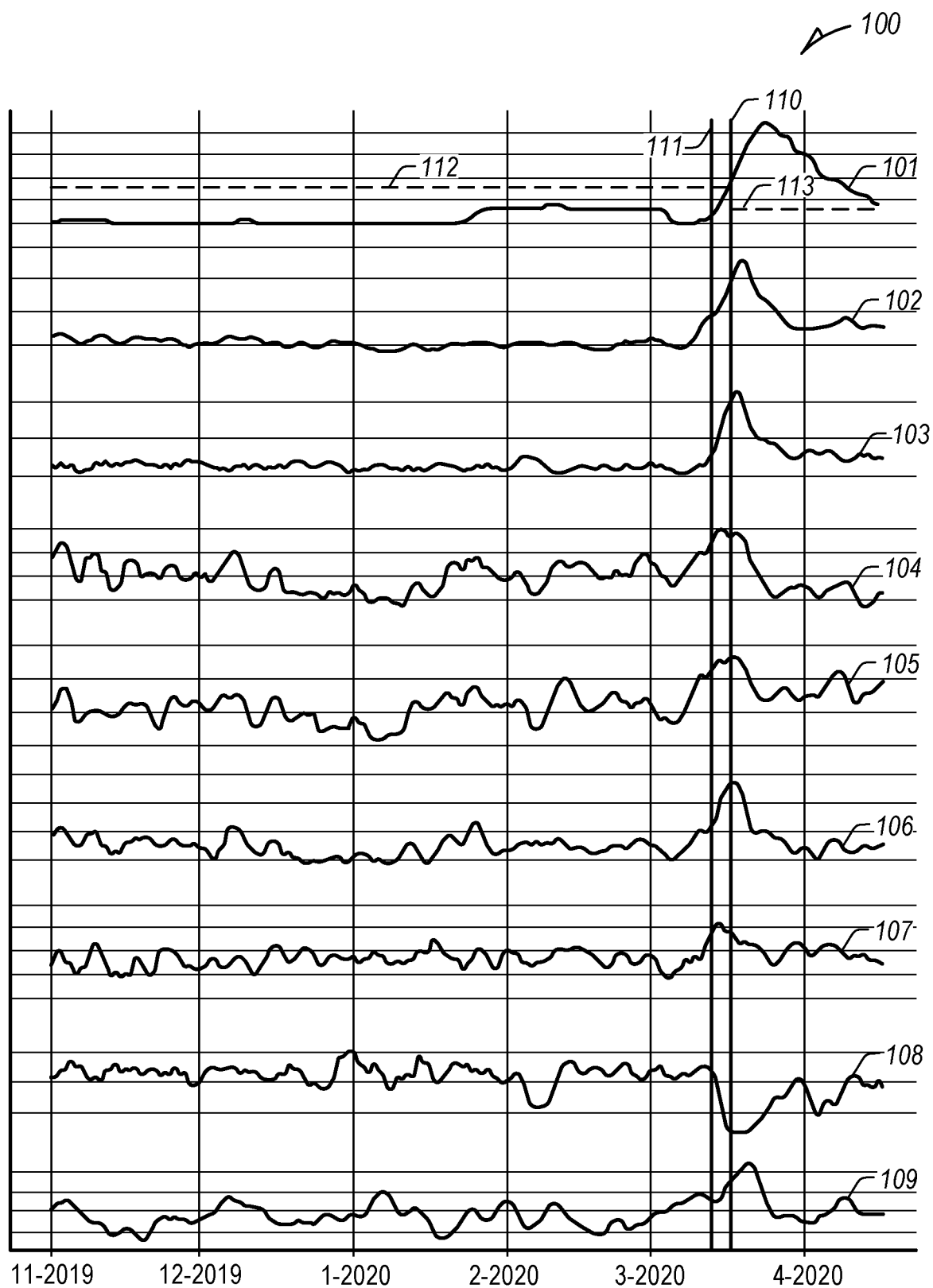
FIG. 1 illustrates an example set of relationships of different physiologic information of a patient.

FIG. 1 illustrates an example set of relationships 100 of different physiologic information of a patient across a number of months (between November 2019 and April 2020), the physiologic information including a HeartLogic™ (HL) index 101, a respiration rate (RR) 102, a rapid shallow breathing index (RSBI) 103, a nighttime heart rate (nHR) 104, a first heart sound (S1) 105, a third heart sound (S3) 106, a patient temperature 107, patient activity 108, and thoracic impedance 109. The amplitudes of each of the physiologic information are different, but illustrate relative changes associated with the patient.

The HL index 101 is an aggregate of measurements from multiple ambulatory sensors, including S1 and S3 heart sounds, thoracic impedance, respiration information, and nighttime heart rate, the aggregate HL index 101 indicative of heart failure changes of the patient over time. The RR 102 is a measure of a breathing rate of the patient. The RSBI 103 is a ratio of respiratory frequency to tidal volume (TV) of the patient. TV can be measured as an aggregate of respiration changes, such as detected using measured changes in thoracic impedance, etc. The nHR 104 is a measure of heart rate (HR) of the patient at night, either in relation to sensing patient sleep or using a preset or selectable time of day corresponding to patient sleep.

Heart sounds are recurring mechanical signals associated with cardiac vibrations from blood flow through the heart with each cardiac cycle and can be separated and classified according to activity associated with the vibrations and blood flow. Heart sounds include four major sounds: the first through the fourth heart sounds (S1, S2, S3, and S4). The first heart sound (S1) 105 is the vibrational sound made by the heart during closure of the atrioventricular (AV) valves, the mitral valve, and the tricuspid valve, at the beginning of systole. The second heart sound (S2) is the vibrational sound made by the heart during closure of the aortic and pulmonary valves at the beginning of diastole. The third heart sound (S3) 106 and the fourth heart sounds (S4) are related to filling pressures of the left ventricle during diastole.

The patient temperature 107 includes an internal patient temperature at an AMD, such as implanted in the thorax of the patient, etc. The patient temperature 107 can be detected using a temperature sensor, such as one or more circuits or electronic components having an electrical characteristic that changes with temperature. The temperature sensor can include a sensing element located on, at, or within the AMD configured to determine a temperature indicative of patient temperature at the location of the AMD.

The patient activity 108 includes an activity measurement of the patient, such as detected using an accelerometer, a posture sensor, or one or more other activity sensors associated with an AMD. The thoracic impedance 109 includes a measure of impedance across a thorax of the patient, such as from one or more electrodes associated with one or more leads of an IMD proximate a heart of the patient and a housing of the IMD implanted subcutaneously at a thoracic location of the patient. In other examples, the thoracic impedance 109 can include one or more other impedance measurements associated with the thorax of the patient.

In FIG. 1, a first alert 110 was issued associated with the HL index 101 crossing an onset threshold 112 (dotted line before the first alert 110). After crossing the onset threshold 112, a reset threshold 113 activates (dotted line after the first alert 110), lower than the onset threshold 112. The specific values of one or both of the onset threshold 112 and the reset threshold 113 can be population-based, specific to the patient based on patient history, as set or established by a physician, or relative to the one or more other values, thresholds, physiologic information, or combinations thereof.

The present inventors have recognized, among other things, that an increase in the patient temperature 107 unexpectedly precedes the rise in the HL index 101 and first alert 110 associated with the HL index 101 crossing the onset threshold. Several days prior to the first alert 110, the patient temperature 107 experienced a peak temperature measurement 111. The rise and corresponding peak in the patient temperature 107 showed a 4-5% increase preceding other physiologic information changes (aside the RR 102) outside a normal or recent variation. In other examples, the rise in the patient temperature 107 can be greater than 4-5%.

The present inventors further recognized that the RR 102 began trending upwards prior to the increase in the patient temperature 107, and continued rising after the peak temperature measurement 111. The change in the RR 102 prior to the rise in the patient temperature 107 was large, illustrating a 25% increase in rate in FIG. 1 over its previous, relatively stable baseline and preceding long-term (e.g., one to three months) range of sensor values. Other sensor values also increased prior to the rise in the patient temperature 107, such as the nHR 104, the S1 105, and the S3 106, but not above their previous ranges over the preceding one to three months (or longer), and not to the percent change extent of the RR 102. The S1 105 and the S3 106 started to trend upwards, but not beyond the change above their previous ranges over the preceding one to three months (or longer) until after the rise in the patient temperature 107. The RR 102 was the only physiologic information from FIG. 1 that preceded the rise in the patient temperature 107 above its previous baseline and preceding long-term (e.g., one to three months) range of sensor values.

Although discussed herein as a preceding one to three months, in certain examples, the patient baseline or previous ranges can be discussed with respect to one or more weeks, or one or more values greater than one to three or five days. The data illustrated in FIG. 1 include dark lines illustrating short-term (e.g., 3-day) averages of physiologic information. Changes in daily values (e.g., representative daily values, such as daily averages, etc.) that go into the short-term values can be larger. Further, as used herein, "large" or "larger" with respect to the relative values of change can refer to a relative change greater than 10% of its previous baseline, or a spike or increase resulting in a value greater than a long-term (e.g., longer than a short-term, such as the preceding week, weeks, one to three months or more) range of sensor values.

The present inventors have recognized, among other things, that a viral-respiratory score can be determined using a specific combination of a first rise in the RR 102 followed in time (e.g., within days, etc.) by a rise in the patient temperature 107, and that an increase in such score can be indicative of patient risk of viral-respiratory disease, or an early indicator of patient viral-respiratory symptoms. In an example, the first rise in the RR 102 can trigger monitoring for a rise in the patient temperature 107. In certain examples, a rise in the patient temperature 107 without a prior or corresponding rise in the RR 102 can be indicative of one or more other conditions separate from viral-respiratory disease (e.g., COVID-19, etc.). Accordingly, comparative diagnostic indicators can be determined, stratified, or confirmed using the specific order of sensor value changes.

In certain examples, the determined viral-respiratory score can be used (such as when the score crosses a threshold or exceeds a baseline by a threshold percentage or amount) to determine or provide an alert (e.g., text, email, web, or other audio or visual indication on a display or patient management device, etc.) to the patient, caregiver, or provider, or a medical device system can manage a relative change in geographic population viral-respiratory scores, such as to allocate system resources to impacted or affected areas, provide one or more population alerts, etc. Population monitoring of viral-respiratory scores, such as in combination with residence or location information, can provide an effective tool to test transmission rates among the general population, allowing geographic management of public spaces. In other examples, the determined viral-respiratory score can be used to change one or more modes of monitoring, processing, data recording or transmission of one or more medical devices or sensors, or to automatically trigger or adjust patient follow-up scheduling.

In other examples, an initial increase in the RR 102 without a corresponding immediate increase in the RSBI 103 can indicate a latent reduction in tidal volume (latent in contrast to the increase in the RR 102), indicating patient chest tightness (e.g., breathlessness or shortness of breath), preceding the rise in the patient temperature 107. In certain examples, such information, alone or in combination with one or more aspects described above, can used to determine or adjust the patient viral-respiratory score.

A decrease in the S1 105 is generally associated with an increased indication of HF. FIG. 1 illustrates an increase in the S1 105 associated with the increase in the RR 102 and the patient temperature 107. Similarly, a decrease in the thoracic impedance 109, indicating patient congestion, is associated with an increased indication of HF. FIG. 1 illustrates an increase in the thoracic impedance 109 associated with the increase in the RR 102 and the patient temperature 107. An increase in the thoracic impedance 109 can be an indication of dry cough. In certain examples, such information, alone or in combination with one or more aspects described above, can used to determine or adjust the patient viral-respiratory score, or to distinguish an indication of viral-respiratory disease from HF.

In certain examples, temporal latency between changes in the RR 102 and the tidal volume change, such as determined using the RSBI 103, can be indicative of viral-respiratory disease severity. Disassociated changes in the RR 102 and the RSBI 103 can be indicative of an increase in disease severity. In certain examples, medical systems can triage patients using the determined viral-respiratory score. In certain examples, triage can be carried out by automatically triggering or adjusting patient follow-up schedules, or providing an alert to a medical device system, such as to contact the patient, to schedule or adjust a follow-up appointment, or to provide an alert to a clinician or caregiver regarding the status of the patient. Due to limited hospital capacity, patients with a lower monitored severity may be advised to recover at home until symptoms worsen, as hospital capacity can otherwise be overwhelmed, impacting patients in most need of assistance.

In an example, a two-phase respiratory response may indicate a transition from adequate respiratory compensation to inadequate compensation. In a first phase, the RR 102 can increase with a constant or relatively constant value of the RSBI 103, in certain examples indicating substantial increases in the RR 102 and tidal volume, indicating an overall unrestricted respiration expansion (adequate respiratory response that is not limited). In a second phase, however, the RR 102 can increase with a sharp increase in the value of the RSBI 103, indicating a constant or decreasing tidal volume. In certain examples, the RR 102 appears to be the sole mechanism of respiratory compensation. Inability to increase tidal volume in the second phase may reflect "chest tightness" that patients complain in the severe stages of viral-respiratory disease.

A time delay between the first and second phases can be a marker of viral-respiratory disease severity or patient risk. A longer delay between the first and second phases can indicate that the patient can handle increased respiratory need without intervention. A short delay between the first and second phases can indicate an increased risk of needing respiratory support. Longer and shorter here can indicate population or patient-specific values, with changes relative to each.

In addition, a median value of the RR 102 remains elevated for weeks during clinical recovery from viral-respiratory disease, suggesting either a slower recovery than noted clinically or long-term impact on HF status.

The systems and methods disclosed herein describe additional capability for existing sensors, allowing existing combinations of sensors to detect, manage, and distinguish additional physiologic conditions and provide system management functions not otherwise previously managed, improving the technological capabilities of a device without increasing the physical cost, e.g., with additional sensors, etc.

In other examples, detection of an indication of viral-respiratory disease, confirmed or not, can be a risk factor for additional later HF events, as recovery from specific viral-respiratory diseases, such as COVID-19, impact patients for a prolonged period of time, for weeks or months after detection of an acute event. Further, viral-respiratory disease, such as COVID-19, can be differentiated from pneumonia or infection, by the rate and scale of change in the patient physiologic information. Pneumonia and infection do not provide changes as quick or as severe as illustrated in FIG. 1. Moreover, thoracic impedance does not increase in pneumonia or infection patients. Accordingly, using the information in FIG. 1, viral-respiratory disease can be differentiated from pneumonia or infection. An AMD, IMD, or other medical device can be configured to change sensor or processing modes, enable or disable specific sensors or combinations of sensors, change sensing frequency of respective sensors, alter power modes, upload frequency to a remote system, etc., using such differentiation, viral-respiratory score, etc.

Figure 2:
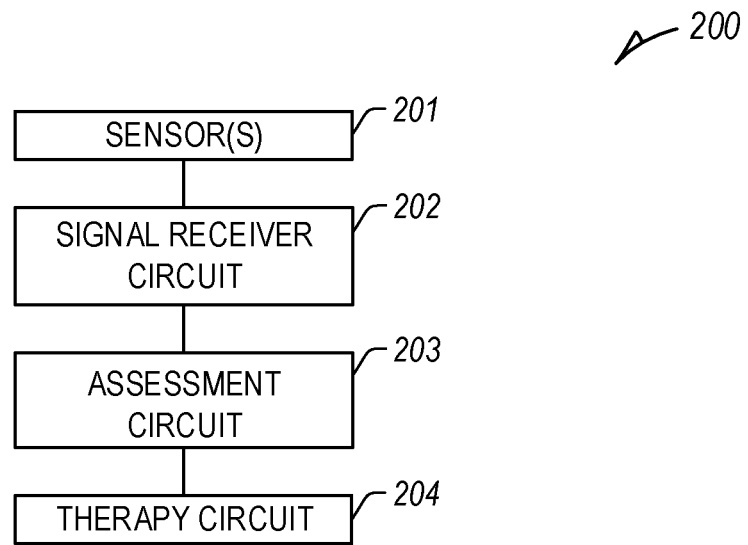
FIG. 2 illustrates an example system, such as a medical device system.

FIG. 2 illustrates an example system 200, such as a medical-device system, etc. In an example, one or more aspects of the example system 200 can be a component of, or communicatively coupled to, an ambulatory medical device (AMD). AMDs can be configured to monitor, detect, or treat various physiologic conditions of the body, such as viral-respiratory disease, etc. AMDs can include a single device or a plurality of medical devices or monitors implanted in a patient's body or otherwise positioned on or about the patient to monitor patient physiologic information of the patient, such as using one or more sensors, the physiologic information including one or more of heart sounds, respiration (e.g., respiration rate, tidal volume (TV), etc.), impedance (e.g., thoracic impedance, cardiac impedance, cutaneous impedance, etc.), pressure (e.g., blood pressure), cardiac activity (e.g., heart rate, cardiac electrical information, etc.), chemical (e.g., electrolyte), physical activity, posture, plethysmography, or one or more other physiologic parameters of a patient, or to provide electrical stimulation or one or more other therapies or treatments to the patient.

The example system 200 can include a signal receiver circuit 202 and an assessment circuit 203. The signal receiver circuit 202 can be configured to receive physiologic information of a patient (or group of patients) from one or more sensors 201. The assessment circuit 203 can be configured to receive information from the signal receiver circuit 202, and to determine one or more parameters (e.g., physiologic parameters, stratifiers, etc.) or patient conditions (e.g., indications of patient dehydration, etc.) using the received physiologic information, such as described herein. The physiologic information can include, among other things, cardiac electrical information, impedance information, respiration information, heart sound information, activity information, posture information, temperature information, chemical information, etc.

In an example, the sensor 201 can include one or more of: a respiration sensor configured to receive respiration information (e.g., a respiration rate, a respiration volume (tidal volume), etc.); an acceleration sensor (e.g., an accelerometer, a microphone, etc.) configured to receive cardiac acceleration information (e.g., cardiac vibration information, pressure waveform information, heart sound information, endocardial acceleration information, acceleration information, activity information, posture information, etc.); an impedance sensor (e.g., intrathoracic impedance sensor, transthoracic impedance sensor, etc.) configured to receive impedance information, a cardiac sensor configured to receive cardiac electrical information; an activity sensor configured to receive information about a physical motion (e.g., activity, steps, etc.); a posture sensor configured to receive posture or position information; a pressure sensor configured to receive pressure information; a plethysmograph sensor (e.g., a photoplethysmography sensor, etc.); a chemical sensor (e.g., an electrolyte sensor, a pH sensor, an anion gap sensor, etc.); a skin temperature sensor; a skin elasticity sensor, or one or more other sensors configured to receive physiologic information of the patient.

The assessment circuit 203 can be configured to provide an output to a user, such as to a display or one or more other user interface, the output including a score, a trend, an alert, or other indication. In other examples, the assessment circuit 203 can be configured to provide an output to another circuit, machine, or process, such as a therapy circuit 204 (e.g., a cardiac resynchronization therapy (CRT) circuit, a chemical therapy circuit, etc.), etc., to control, adjust, or cease a therapy of a medical device, a drug delivery system, etc., or otherwise alter one or more processes or functions of one or more other aspects of a medical-device system, such as one or more CRT parameters, drug delivery, dosage determinations or recommendations, etc. In an example, the therapy circuit 204 can include one or more of a stimulation control circuit, a cardiac stimulation circuit, a dosage determination or control circuit, etc. In other examples, the therapy circuit 204 can be controlled by the assessment circuit 203, or one or more other circuits, etc.

The assessment circuit 203 can be configured to determine an indication of patient condition, such as one or more scores indicative of patient condition (e.g., a viral-respiratory score, a heart failure score, etc.), a presence or absence of a medical event (e.g., an arrhythmia event or potential arrhythmia event), an indication of patient hydration, dehydration, worsening dehydration status, an indication of patient vomiting, an indication of patient diarrhea, etc., using the received physiologic information.

AMDs can include a range of medical devices, including, for example, traditional cardiac rhythm management (CRM) devices, such as pacemakers, defibrillators, or cardiac resynchronizers, include implantable or subcutaneous devices configured to be implanted in a chest of a patient. The CRM device can include one or more leads to position one or more electrodes or other sensors at various locations in or near the heart, such as in one or more of the atria or ventricles. Separate from, or in addition to, the one or more electrodes or other sensors of the leads, the CRM device can include one or more electrodes or other sensors (e.g., a pressure sensor, an accelerometer, a gyroscope, a microphone, etc.) powered by a power source in the CRM device. The one or more electrodes or other sensors of the leads, the CRM device, or a combination thereof, can be configured detect physiologic information from the patient, or provide one or more therapies or stimulation to the patient, such as Implantable devices can additionally or separately include leadless cardiac pacemakers (LCP), small (e.g., smaller than traditional implantable CRM devices, in certain examples having a volume of about 1 cc, etc.), self-contained devices including one or more sensors, circuits, or electrodes configured to monitor physiologic information (e.g., heart rate, etc.) from, detect physiologic conditions (e.g., tachycardia) associated with, or provide one or more therapies or stimulation to the heart without traditional lead or implantable CRM device complications (e.g., required incision and pocket, complications associated with lead placement, breakage, or migration, etc.). In certain examples, an LCP can have more limited power and processing capabilities than a traditional CRM device; however, multiple LCP devices can be implanted in or about the heart to detect physiologic information from, or provide one or more therapies or stimulation to, one or more chambers of the heart. The multiple LCP devices can communicate between themselves, or one or more other implanted or external devices.

Each additional sensor within or associated with an AMD or medical device system can increase system cost and complexity, reduce system reliability, or increase the power consumption and reduce the usable life of the AMD. Accordingly, it can be beneficial to use a single sensor to determine multiple types of physiologic information, or a smaller number of sensors to measure a larger number of different types of physiologic information. For example, it can be beneficial to detect atrial cardiac electrical information without a lead or an electrode in, or in contact with, the atria.

Figure 3:
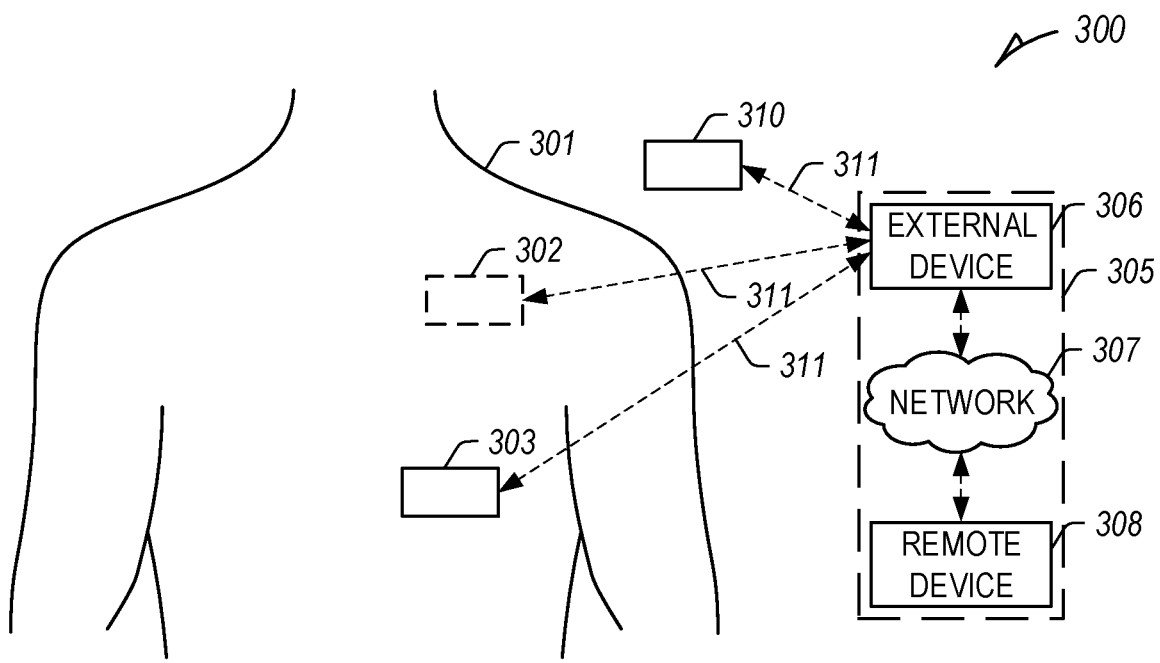
FIG. 3 illustrates an example patient management system and portions of an environment in which the system may operate.

FIG. 3 illustrates an example patient management system 300 and portions of an environment in which the system 300 may operate. The patient management system 300 can perform a range of activities, including remote patient monitoring and diagnosis of a disease condition. Such activities can be performed proximal to a patient 301, such as in a patient home or office, through a centralized server, such as in a hospital, clinic, or physician office, or through a remote workstation, such as a secure wireless mobile computing device.

The patient management system 300 can include one or more AMDs, an external system 305, and a communication link 311 providing for communication between the one or more AMDs and the external system 305. The one or more AMDs can include an implantable medical device (IMD) 302, a wearable medical device 303, or one or more other implantable, leadless, subcutaneous, external, wearable, or AMDs configured to monitor, sense, or detect information from, determine physiologic information about, or provide one or more therapies to treat various conditions of the patient 301, such as one or more cardiac or non-cardiac conditions (e.g., dehydration, etc.).

In an example, the IMD 302 can include one or more traditional cardiac rhythm management (CRM) devices, such as a pacemaker or defibrillator, implanted in a chest of a patient, having a lead system including one or more transveous, subcutaneous, or non-invasive leads or catheters to position one or more electrodes or other sensors (e.g., a heart sound sensor) in, on, or about a heart or one or more other position in a thorax, abdomen, or neck of the patient 301. In another example, the IMD 302 can include a monitor implanted, for example, subcutaneously in the chest of patient 301.

The IMD 302 can include an assessment circuit configured to detect or determine specific physiologic information of the patient 301, or to determine one or more conditions or provide information or an alert to a user, such as the patient 301 (e.g., a patient), a clinician, or one or more other caregivers or processes. The IMD 302 can alternatively or additionally be configured as a therapeutic device configured to treat one or more medical conditions of the patient 301. The therapy can be delivered to the patient 301 via the lead system and associated electrodes or using one or more other delivery mechanisms. The therapy can include delivery of one or more drugs to the patient 301 using the IMD 302 or one or more of the other AMDs. In some examples, therapy can include CRT for rectifying dyssynchrony and improving cardiac function in CHF patients. In other examples, the IMD 302 can include a drug delivery system, such as a drug infusion pump to deliver drugs to the patient for managing arrhythmias or complications from arrhythmias, hypertension, or one or more other physiologic conditions.

The wearable medical device 303 can include one or more wearable or external medical sensors or devices (e.g., automatic external defibrillators (AEDs), Holter monitors, patch-based devices, smart watches, smart accessories, wrist- or finger-worn medical devices, such as a finger-based photoplethysmography sensor, etc.). The wearable medical device 303 can include an optical sensor configured to detect a PPG signal on a wrist, finger, or other location on the patient 301. In other examples, the wearable medical device 303 can include an acoustic sensor or accelerometer to detect acoustic information (e.g., heart sounds) or the sound or vibration of blood flow, an impedance sensor to detect impedance variations associated with changes in blood flow or volume, a temperature sensor to detect temperature variation associated with blood flow, a laser Doppler vibrometer or other pressure, strain, or physical sensor to detect physical variations associated with blood flow, etc.

The patient management system 300 can include, among other things, a respiration sensor configured to receive respiration information (e.g., a respiration rate, a respiration volume (a minute volume (MV), a tidal volume (TV), etc.), etc.), a heart sound sensor configured to receive heart sound information, a thoracic impedance sensor configured to receive impedance information, a cardiac sensor configured to receive cardiac electrical information, an activity sensor configured to receive information about a physical motion (e.g., activity, posture, etc.), a plethysmography sensor, or one or more other sensors configured to receive physiologic information of the patient 301.

The external system 305 can include a dedicated hardware/software system, such as a programmer, a remote server-based patient management system, or alternatively a system defined predominantly by software running on a standard personal computer. The external system 305 can manage the patient 301 through the IMD 302 or one or more other AMDs connected to the external system 305 via a communication link 311. In other examples, the IMD 302 can be connected to the wearable device 303, or the wearable device 303 can be connected to the external system 305, via the communication link 311. This can include, for example, programming the IMD 302 to perform one or more of acquiring physiological data, performing at least one self-diagnostic test (such as for a device operational status), analyzing the physiological data to detect a cardiac arrhythmia, or optionally delivering or adjusting a therapy to the patient 301. Additionally, the external system 305 can send information to, or receive information from, the 1 MB 302 or the wearable device 303 via the communication link 311. Examples of the information can include real-time or stored physiological data from the patient 301, diagnostic data, such as detection of patient hydration status, hospitalizations, responses to therapies delivered to the patient 301, or device operational status of the 1 MB 302 or the wearable device 303 (e.g., battery status, lead impedance, etc.). The communication link 311 can be an inductive telemetry link, a capacitive telemetry link, or a radio-frequency (RF) telemetry link, or wireless telemetry based on, for example, "strong" Bluetooth® or IEEE 802.11 wireless fidelity "Wi-Fi" interfacing standards. Other configurations and combinations of patient data source interfacing are possible.

By way of example and not limitation, the external system 305 can include an external device 306 in proximity of the one or more AMDs, and a remote device 308 in a location relatively distant from the one or more AMDs, in communication with the external device 306 via a communication network 307. Examples of the external device 306 can include a medical device programmer.

The remote device 308 can be configured to evaluate collected patient or patient information and provide alert notifications, among other possible functions. In an example, the remote device 308 can include a centralized server acting as a central hub for collected data storage and analysis. The server can be configured as a uni-, multi-, or distributed computing and processing system. The remote device 308 can receive data from multiple patients. The data can be collected by the one or more AMDs, among other data acquisition sensors or devices associated with the patient 301. The server can include a memory device to store the data in a patient database. The server can include an alert analyzer circuit to evaluate the collected data to determine if specific alert condition is satisfied. Satisfaction of the alert condition may trigger a generation of alert notifications, such to be provided by one or more human-perceptible user interfaces. In some examples, the alert conditions may alternatively or additionally be evaluated by the one or more AMDs, such as the IMD. By way of example, alert notifications can include a Web page update, phone or pager call, E-mail, SMS, text or "Instant" message, as well as a message to the patient and a simultaneous direct notification to emergency services and to the clinician. Other alert notifications are possible. The server can include an alert prioritizer circuit configured to prioritize the alert notifications. For example, an alert of a detected medical event can be prioritized using a similarity metric between the physiological data associated with the detected medical event to physiological data associated with the historical alerts.

The remote device 308 may additionally include one or more locally configured clients or remote clients securely connected over the communication network 307 to the server. Examples of the clients can include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 308, including the server and the interconnected clients, may also execute a follow-up scheme by sending follow-up requests to the one or more AMDs, or by sending a message or other communication to the patient 301 (e.g., the patient), clinician or authorized third party as a compliance notification.

The communication network 307 can provide wired or wireless interconnectivity. In an example, the communication network 307 can be based on the Transmission Control Protocol/Internet Protocol (TCP/IP) network communication specification, although other types or combinations of networking implementations are possible. Similarly, other network topologies and arrangements are possible.

One or more of the external device 306 or the remote device 308 can output the detected medical events to a system user, such as the patient or a clinician, or to a process including, for example, an instance of a computer program executable in a microprocessor. In an example, the process can include an automated generation of recommendations for anti-arrhythmic therapy, or a recommendation for further diagnostic test or treatment. In an example, the external device 306 or the remote device 308 can include a respective display unit for displaying the physiological or functional signals, or alerts, alarms, emergency calls, or other forms of warnings to signal the detection of arrhythmias. In some examples, the external system 305 can include an external data processor configured to analyze the physiological or functional signals received by the one or more AMDs, and to confirm or reject the detection of arrhythmias. Computationally intensive algorithms, such as machine-learning algorithms, can be implemented in the external data processor to process the data retrospectively to detect cardia arrhythmias.

Portions of the one or more AMDs or the external system 305 can be implemented using hardware, software, firmware, or combinations thereof. Portions of the one or more AMDs or the external system 305 can be implemented using an application-specific circuit that can be constructed or configured to perform one or more functions or can be implemented using a general-purpose circuit that can be programmed or otherwise configured to perform one or more functions. Such a general-purpose circuit can include a microprocessor or a portion thereof, a microcontroller or a portion thereof, or a programmable logic circuit, a memory circuit, a network interface, and various components for interconnecting these components. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. "Sensors" can include electronic circuits configured to receive information and provide an electronic output representative of such received information.

The patient management system 300 can include a therapy device 310, such as a drug delivery device configured to provide therapy or therapy information (e.g., dosage information, etc.) to the patient 301, such as using information from one or more of the AMDs. In other examples, one or more of the AMDs can be configured to provide therapy or therapy information to the patient 301. The therapy device 310 can be configured to send information to or receive information from one or more of the AMDs or the external system 305 using the communication link 311. In an example, the one or more AMDs, the external device 306, or the remote device 308 can be configured to control one or more parameters of the therapy device 310.

The external system 305 can allow for programming the one or more AMDs and can receives information about one or more signals acquired by the one or more AMDs, such as can be received via a communication link 311. The external system 305 can include a local external IMD programmer. The external system 305 can include a remote patient management system that can monitor patient status or adjust one or more therapies such as from a remote location.

The assessment circuit may be implemented at the external system 305, which can be configured to perform HF risk stratification such as using data extracted from the one or more AMDs or data stored in a memory within the external system 305. Portions of patient chronic condition-based HF or other assessment circuit may be distributed between the one or more AMDs and the external system 305.

Figure 4:
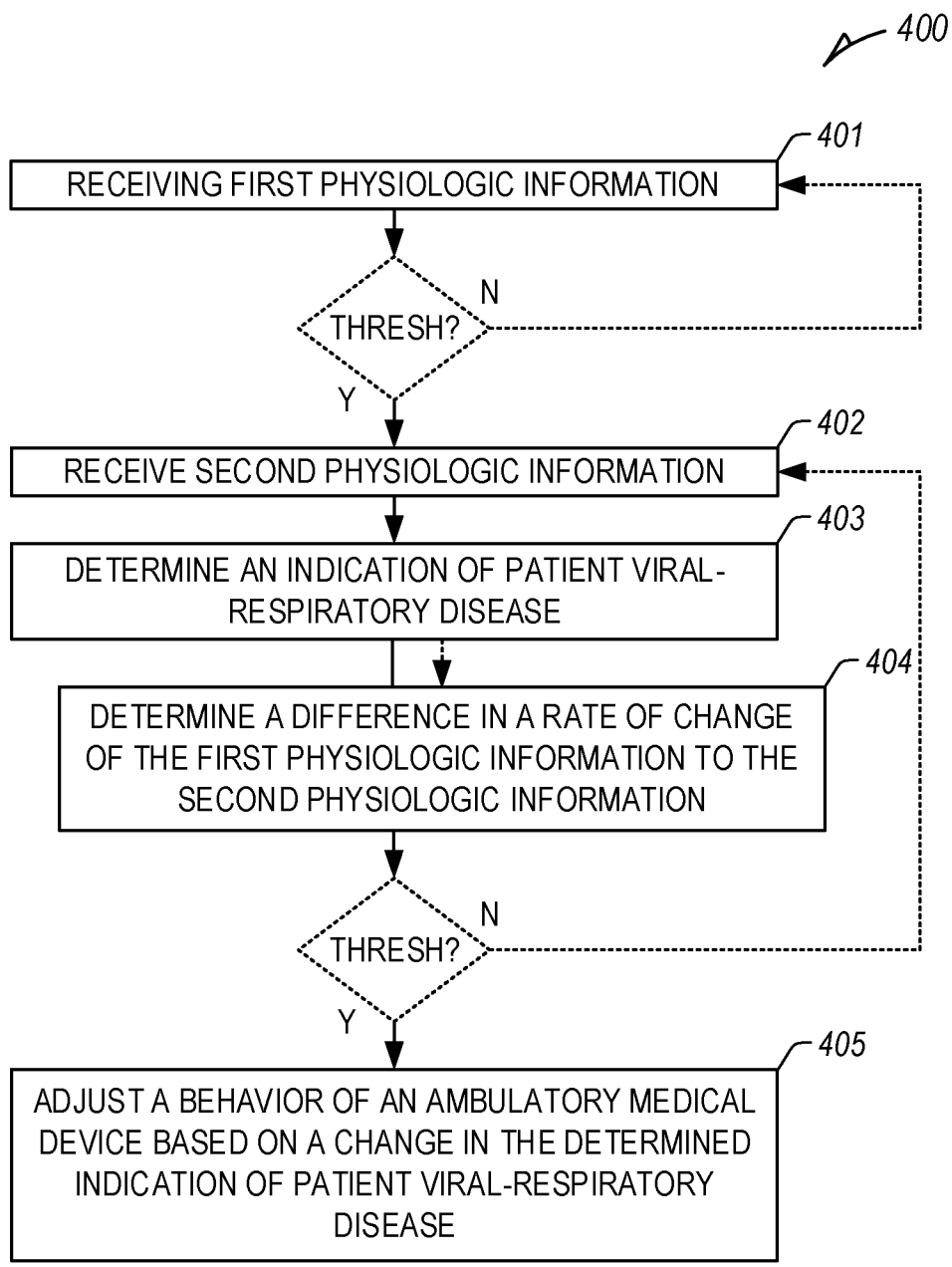
FIG. 4 illustrates an example method to determine an indication of patient viral-respiratory disease.

FIG. 4 illustrates an example method 400 to determine an indication of patient viral-respiratory disease. At 401, first physiologic information of a patient can be received, such as using a signal receiver circuit. The first physiologic information can include respiration information of the patient. In an example, the respiration information can include one or more of a respiration rate (RR), a rapid shallow breathing index (RSBI), a tidal volume (TV), etc., of the patient. The respiration information of the patient can be received or determined from a respiration signal of the patient, including, for example, changes in acceleration, impedance, or airflow changes of the patient indicative of patient respiration. The respiration information can be sensed from one or more of a respiration sensor, an impedance sensor, an accelerometer, or an airflow sensor. Each sensor has different power requirements, and certain sensors, such as the impedance sensor or the accelerometer, can be used to detect other information in addition to respiration information at the same time as sensing respiration information or at different times, depending on resource allocation, desired medical information, etc.

In other examples, the first physiologic information can include one or more types of physiologic information different than respiration information, such as heart sounds information, patient temperature information, activity information, thoracic impedance information, heart rate information, nighttime heart rate information, or one or more other physiologic measurements or an aggregate of measurements from multiple ambulatory sensors, such as the HL index, etc.

The first physiologic information can include a single measurement, an ensemble value of multiple measurements (e.g., between 2 and 5, 2 and 10, 2 and 20, in certain examples, with an upper limit covering less than half of a day, etc.), a daily value (or a portion of a day, such as daytime, nighttime, morning, afternoon, evening, etc.), a short-term value (e.g., covering between 2 and 5 days, 2 and 7 days, etc.), a long-term value (e.g., a longer time period than the short-term, typically at least double the short-term value, covering between 1 and 2 weeks, 2 weeks to a month, 1 to 3 months, etc., in certain examples preceding and not overlapping the short-term period), a composite measure of multiple values or different physiologic information, or a relative measure of one or more of these values, such as with respect to another one or more of these values or different physiologic information, etc.

In an example, the first physiologic information can optionally be compared to one or more thresholds, such as a first threshold. In an example, the first threshold can include a population-based value, a patient-specific value, or a value indicative of a relative increase in the first physiologic information of the patient, etc. In certain examples, if the first physiologic information exceeds the first threshold, the method 400 can proceed, whereas if the first physiologic information does not exceed the first threshold, the method 400 returns to 401.

At 402, second physiologic information can be received, such as using the signal receiver circuit. The second physiologic information can include one or more types of physiologic information different than the first physiologic information, such as heart sounds information, patient temperature, activity information, thoracic impedance, heart rate, nighttime heart rate, or one or more other physiologic measurements or an aggregate of measurements from multiple ambulatory sensors, such as the HL index, etc. In an example, if the first physiologic information does not include respiration information, the second physiologic information can include respiration information, or if the first physiologic information includes one type of respiration information (e.g., the RR), the second physiologic information can include one or more other types of respiration information (e.g., the TV, the RSBI, etc.).

Similar to that described above with respect to the first measurement, the second physiologic information can include a single measurement, an ensemble value of multiple measurements, a daily value, a short-term value, a long-term value, a composite measure, or a relative measure of one or more of these values or different physiologic information, etc.

At 403, an indication of patient viral-respiratory disease (VRd) can be determined, such as by an assessment circuit, using the first and second physiologic information. In an example, the VRd can be determined as a function of the first and second physiologic information. For example, if the first physiologic information includes respiration information of the patient, such as the RR, and the second physiologic information includes temperature information, such as patient temperature (T), one example function can include:

$$VRd \propto aT + bRR \quad (1)$$

In other examples, the VRd can be determined using one or more other functions of the RR and the T, or one or more other functions of one or more other combinations of first and second physiologic information.

In an example, the VRd can be determined using the second physiologic information in response to the first physiologic information meeting a predetermined criterion, such as the first physiologic information exceeding the first threshold, etc. In an example, the assessment circuit may not determine the indication of patient viral-respiratory disease at all times, but instead when the first physiologic information meets the predetermined criterion, comparatively reducing processing time, power consumption, data transmission between components, etc. In other examples, the second physiologic information may not be received until the first physiologic information exceeds the first threshold, such that sensing or receiving the second physiologic information can be triggered by a change in the first physiologic information, comparatively reducing processing time, power consumption, data transmission between components, etc.

In an example, the VRd can be determined using the first physiologic information of a first time period and the second physiologic information of a second time period different than the first time period. In certain examples, the first and second time periods can be overlapping, such that the first time period at least partially overlaps the second time period, or non-overlapping, such that the first time period entirely precedes the second time period.

In an example, the first physiologic information can include the RR of the patient and the second physiologic information can include the T of the patient, and the VRd can be determined as a function of an increase in the T of the patient in response to an increase in the RR of the patient exceeding a threshold amount (e.g., such as 20% or 25% of the short- or long-term value, etc.). One example function can include:

$$\text{if } \Delta RR \geq X, \text{ then } VRd \propto \Delta T \quad (2)$$

In an example, the increase in the RR can include a relative increase in the RR determined using a difference between a current RR value of the patient and a RR baseline of the patient. In certain examples, the threshold amount (X) can be a function of the RR baseline. In certain examples, the RR baseline can include a long-term value, or a short-term value if the current RR value covers a period more recent or shorter than the short-term value.

Similarly, in an example, the increase in the T can include a relative increase the patient temperature information determined using a difference between a current T value of the patient and a T baseline of the patient.

In certain examples, the long-term, short-term, or baseline values can be determined as an average value of a number of previous samples (e.g., ($\bar{x}$)). For example, with respect to the RR:

$$RR(\bar{x}) = \frac{1}{b-a} \int_a^b RR(x)dx.$$

The average respiration rate can be a function of the average of a number of samples between a and b, where a and b vary depending on the type of average (e.g., short-term, long-term, aggregate baseline, etc.). Example functions of ΔRR and ΔT can include:

$$\Delta RR = RR(\alpha) - RR(\bar{x}), \quad \text{or} \quad \frac{RR(\alpha) - RR(\bar{x})}{RR(\bar{x})} \quad (3)$$

$$\Delta T = T(\beta) - T(\bar{y}), \quad \text{or} \quad \frac{T(\beta) - T(\bar{y})}{T(\bar{y})} \quad (4)$$

At 404, a difference in a rate of change of the first physiologic information to the second physiologic information can be determined, and the VRd can be determined using the determined difference in the rate of change. Example functions can include:

$$VRd \propto \frac{\Delta RR}{\Delta S3} \quad (5)$$

An example function of ΔS3 can include:

$$\Delta S3 = S3(\beta) - S3(\bar{y}), \text{ or}$$

$$\frac{S3(\beta) - S3(\bar{y})}{S3(\bar{y})}$$

Other example functions of VRd as a difference in the rate of change of the first and second physiologic information can include:

$$VRd \propto \frac{\Delta RR}{\Delta RSBI} \quad (7)$$

$$VRd \propto \frac{\Delta RR}{\Delta TV} \quad (8)$$

In an example, the VRd can optionally be compared to one or more thresholds, such as a second threshold. In an example, the second threshold can include a population-based value, a patient-specific value, or a value indicative of a relative increase in the VRd of the patient (e.g., a relative increase in the VRd of the patient, such as a 20% increase, a 25% increase, etc.), etc. In certain examples, if the VRd exceeds the second threshold, the method 400 can proceed, whereas if the VRd does not exceed the second threshold, the method 400 returns to 402 or optionally to 401.

At 405, a behavior of an ambulatory medical device can be adjusted, such as using the assessment circuit, based on a change in the determined VRd. For example, when the VRd exceeds the second threshold, such as a population-based or patient-based threshold indicating that the patient is at risk or an increased risk of a viral-respiratory disease, the assessment circuit can automatically transition an AMD from a normal operation mode to an alert mode. The assessment circuit can be configured to automatically provide an alert associated with the determined VRd to or display the alert on one or more components of a patient management system. In certain examples, the alert mode can include an enhanced monitoring mode by one or more sensors or circuits of an AMD, etc., including one or more of (in contrast to the normal operation mode) an increased sensing frequency, increased processing resources (e.g., reducing the time period between successive determinations of indications of patient viral-respiratory disease, determining indications of patient viral-respiratory disease using more or different physiologic information, etc.), increased communication resources (e.g., transmitting more information from the AMD to one or more other components of the patient management system, or transmitting information more frequently), increased storage of physiologic information, etc., each of which consume more power resources at the AMD. Accordingly, it is important to not always be in such an alert mode unless necessary.

Figure 5:
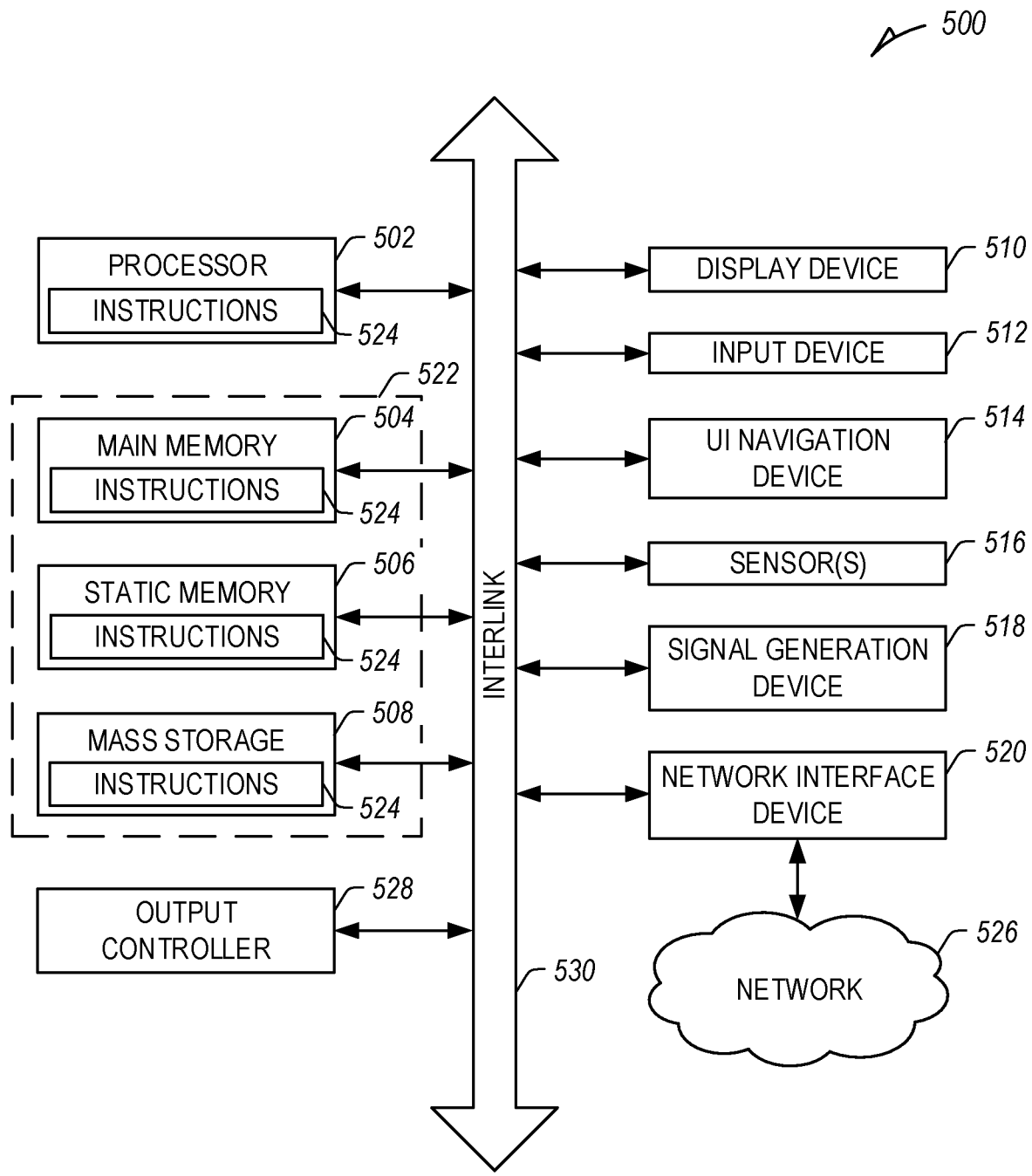
FIG. 5 illustrates a block diagram of an example machine upon which any one or more of the techniques (e.g., methodologies) discussed herein may perform.

FIG. 5 illustrates a block diagram of an example machine 500 upon which any one or more of the techniques (e.g., methodologies) discussed herein may perform. Portions of this description may apply to the computing framework of one or more of the medical devices described herein, such as the AMD, the IMD, the external programmer, etc. Further, as described herein with respect to medical device components, systems, or machines, such may require regulatory-compliance not capable by generic computers, components, or machinery.

Examples, as described herein, may include, or may operate by, logic or a number of components, or mechanisms in the machine 500. Circuitry (e.g., processing circuitry, an assessment circuit, etc.) is a collection of circuits implemented in tangible entities of the machine 500 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 500 follow.

In alternative embodiments, the machine 500 may operate as a standalone device or may be connected (e.g., networked) to other machines. In a networked deployment, the machine 500 may operate in the capacity of a server machine, a client machine, or both in server-client network environments. In an example, the machine 500 may act as a peer machine in peer-to-peer (P2P) (or other distributed) network environment. The machine 500 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 500 may include a hardware processor 502 (e.g., a central processing unit (CPU), a graphics processing unit (GPU), a hardware processor core, or any combination thereof), a main memory 504, a static memory (e.g., memory or storage for firmware, microcode, a basic-input-output (BIOS), unified extensible firmware interface (UEFI), etc.) 506, and mass storage 508 (e.g., hard drive, tape drive, flash storage, or other block devices) some or all of which may communicate with each other via an interlink (e.g., bus) 530. The machine 500 may further include a display unit 510, an alphanumeric input device 512 (e.g., a keyboard), and a user interface (UI) navigation device 514 (e.g., a mouse). In an example, the display unit 510, input device 512, and UI navigation device 514 may be a touch screen display. The machine 500 may additionally include a signal generation device 518 (e.g., a speaker), a network interface device 520, and one or more sensors 516, such as a global positioning system (GPS) sensor, compass, accelerometer, or one or more other sensors. The machine 500 may include an output controller 528, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 502, the main memory 504, the static memory 506, or the mass storage 508 may be, or include, a machine-readable medium 522 on which is stored one or more sets of data structures or instructions 524 (e.g., software) embodying or utilized by any one or more of the techniques or functions described herein. The instructions 524 may also reside, completely or at least partially, within any of registers of the processor 502, the main memory 504, the static memory 506, or the mass storage 508 during execution thereof by the machine 500. In an example, one or any combination of the hardware processor 502, the main memory 504, the static memory 506, or the mass storage 508 may constitute the machine-readable medium 522. While the machine-readable medium 522 is illustrated as a single medium, the term "machine-readable medium" may include a single medium or multiple media (e.g., a centralized or distributed database, and/or associated caches and servers) configured to store the one or more instructions 524.

The term "machine-readable medium" may include any medium that is capable of storing, encoding, or carrying instructions for execution by the machine 500 and that cause the machine 500 to perform any one or more of the techniques of the present disclosure, or that is capable of storing, encoding, or carrying data structures used by or associated with such instructions. Non-limiting machine-readable medium examples may include solid-state memories, optical media, magnetic media, and signals (e.g., radio frequency signals, other photon-based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 524 may be further transmitted or received over a communications network 526 using a transmission medium via the network interface device 520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 520 may include one or more physical jacks (e.g., Ethernet, coaxial, or phone jacks) or one or more antennas to connect to the communications network 526. In an example, the network interface device 520 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 500, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments. Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system comprising:
a signal receiver circuit configured to receive first and second physiologic information of a patient, the first physiologic information comprising respiration rate information of the patient and the second physiologic information comprising temperature information of the patient different than the first physiologic information; and
an assessment circuit configured to:
determine a relative change in the respiration rate information of the patient over a first time period;
in response to the determined relative change in the respiration rate information over the first time period exceeding a first threshold, determine a change in the temperature information of the patient over a second time period different than the first time period;
determine an indication of patient viral-respiratory disease as a function of the determined change in the temperature information of the patient over the second time period in response to the determined relative change in the respiration rate information over the first time period exceeding the first threshold; and
in response to the determined indication of the patient viral-respiratory disease exceeding a second threshold, provide a viral-respiratory alert to a user or process to change a mode of a component of the system or to trigger or adjust patient follow-up scheduling.

2. The system of claim 1, wherein the assessment circuit is configured to determine the indication of the patient viral-respiratory disease using a difference in a rate of change of the first physiologic information to the second physiologic information.

3. The system of claim 1, wherein the assessment circuit is configured to determine the indication of patient viral-respiratory disease using the second physiologic information in response to the first physiologic information meeting a predetermined criterion.

4. The system of claim 1, wherein the first time period precedes and is non-overlapping with the second time period.

5. The system of claim 1, wherein the assessment circuit is configured to determine the relative increase in the respiration rate information using a difference between the received respiration rate information of the patient and a respiration rate baseline of the patient, wherein the threshold amount is a function of the respiration rate baseline,
wherein the increase in the temperature information comprises a relative increase the temperature information, and
wherein the assessment circuit is configured to determine the relative increase in the temperature information using a difference between the received temperature information of the patient and a temperature baseline of the patient.

6. The system of claim 5, wherein the assessment circuit is configured to determine the respiration rate baseline of the patient using the received respiration rate information of the patient over the first time period, and to determine the temperature baseline of the patient using the received respiration rate information of the patient over the second time period.

7. The system of claim 1, wherein the system comprises an ambulatory medical device comprising a respiration sensor configured to sense respiration rate information of the patient, and
wherein the ambulatory medical device is configured to adjust a behavior of the ambulatory medical device based on a change in the determined indication of the patient viral-respiratory disease.

8. The system of claim 1, comprising an implantable medical device including a respiration sensor configured to sense respiration rate information of the patient and a temperature sensor configured to sense the temperature information of the sensor.

9. The system of claim 8, wherein the implantable medical device includes the signal receiver circuit and the assessment circuit.

10. A method comprising:
receiving, using a signal receiver circuit, first and second physiologic information of a patient, the first physiologic information comprising respiration rate information of the patient, and the second physiologic information comprising temperature information of the patient different than the first physiologic information; and
determining, using an assessment circuit, a relative change in the respiration rate information of the patient over a first time period;
in response to the determined relative change in the respiration rate information over the first time period exceeding a first threshold, determining a change in the temperature information of the patient over a second time period different than the first time period;
determining, using the assessment circuit, an indication of patient viral-respiratory disease as a function of the determined change in the temperature information of the patient over the second time period in response to the determined relative change in the respiration rate information over the first time period exceeding the first threshold; and
in response to the determined indication of the patient viral-respiratory disease exceeding a second threshold, providing a viral-respiratory alert to a user or process to change a mode of a component of the system or to trigger or adjust patient follow-up scheduling.

11. The method of claim 10, wherein the determining the indication of the patient viral-respiratory disease comprises using a difference in a rate of change of the first physiologic information to the second physiologic information.

12. The method of claim 10, wherein the determining the indication of the patient viral-respiratory disease comprises using the second physiologic information in response to the first physiologic information meeting a predetermined criterion.

13. The method of claim 10, wherein the first time period precedes and is non-overlapping with the second time period.

14. The method of claim 10, wherein the determining the relative increase in the respiration rate information comprises using a difference between the received respiration rate information of the patient and a respiration rate baseline of the patient, wherein the threshold amount is a function of the respiration rate baseline,
wherein the increase in the temperature information comprises a relative increase the temperature information, and
wherein the assessment circuit is configured to determine the relative increase in the temperature information using a difference between the received temperature information of the patient and a temperature baseline of the patient.

15. The method of claim 14, comprising:
  determining, using the assessment circuit, the respiration rate baseline of the patient using the received respiration rate information of the patient over the first time period; and
  determining, using the assessment circuit, the temperature baseline of the patient using the received respiration rate information of the patient over the second time period.

16. The method of claim 10, comprising:
  sensing, using a respiration sensor of an ambulatory medical device, respiration information of the patient and determining the respiration rate information of the patient; and
  adjusting, using a control circuit of the ambulatory medical device, a behavior of the ambulatory medical device based on a change in the determined indication of the patient viral-respiratory disease.

17. A system comprising:
  means for receiving first and second physiologic information of a patient, the first physiologic information comprising respiration rate information of the patient, and the second physiologic information comprising temperature information of the patient different than the first physiologic information; and
  means for determining a relative change in the respiration rate information of the patient over a first time period;
  means for determining, in response to the determined relative change in the respiration rate information over the first time period exceeding a first threshold, a change in the temperature information of the patient over a second time period different than the first time period;
  means for determining an indication of patient viral-respiratory disease as a function of the determined change in the temperature information of the patient over the second time period in response to the determined relative change in the respiration rate information over the first time period exceeding the first threshold; and
  means for providing, in response to the determined indication of the patient viral-respiratory disease exceeding a second threshold, a viral-respiratory alert to a user or process to change a mode of a component of the system or to trigger or adjust patient follow-up scheduling.

18. The system of claim 17, wherein the first time period precedes and is non-overlapping with the second time period.

\* \* \* \* \*